United States Patent [19]
Bainton

[11] Patent Number: 4,705,024
[45] Date of Patent: Nov. 10, 1987

[54] LARYNGOSCOPE FOR USE WITH PHARYNGEAL OBSTRUCTIONS

[76] Inventor: Cedric R. Bainton, 50 Ventura, San Francisco, Calif. 94116

[21] Appl. No.: 876,816

[22] Filed: Jun. 20, 1986

[51] Int. Cl.⁴ .............................................. A61B 1/26
[52] U.S. Cl. ........................................ 128/11; 128/16
[58] Field of Search ...................... 128/10, 11, 15, 16, 128/17, 18, 6

[56] References Cited

U.S. PATENT DOCUMENTS

| 2,756,742 | 7/1956 | Barton | 128/15 |
|---|---|---|---|
| 2,797,683 | 7/1957 | Aiken | 128/6 |
| 3,856,001 | 12/1974 | Phillips | 128/11 |
| 4,126,127 | 11/1978 | May | 128/11 |
| 4,295,465 | 10/1981 | Racz et al. | 128/11 |
| 4,337,761 | 7/1982 | Upsher | 128/11 |
| 4,360,008 | 11/1982 | Corazella, Jr. | 128/11 |
| 4,425,909 | 1/1984 | Rieser | 128/16 |
| 4,681,094 | 7/1987 | Rolnick | 128/10 |

FOREIGN PATENT DOCUMENTS

| 612116 | 11/1948 | United Kingdom | 128/11 |
|---|---|---|---|
| 806467 | 12/1958 | United Kingdom | 128/11 |

Primary Examiner—William H. Grieb
Attorney, Agent, or Firm—Glen R. Grunewald; Thomas R. Lampe

[57] ABSTRACT

A laryngoscope blade including a rear trough-like portion and a forward tubular portion with the tubular portion having a beveled end and being between 5 and 8.5 centimeters in length, and with a light source located in the interior of the tubular portion.

3 Claims, 3 Drawing Figures

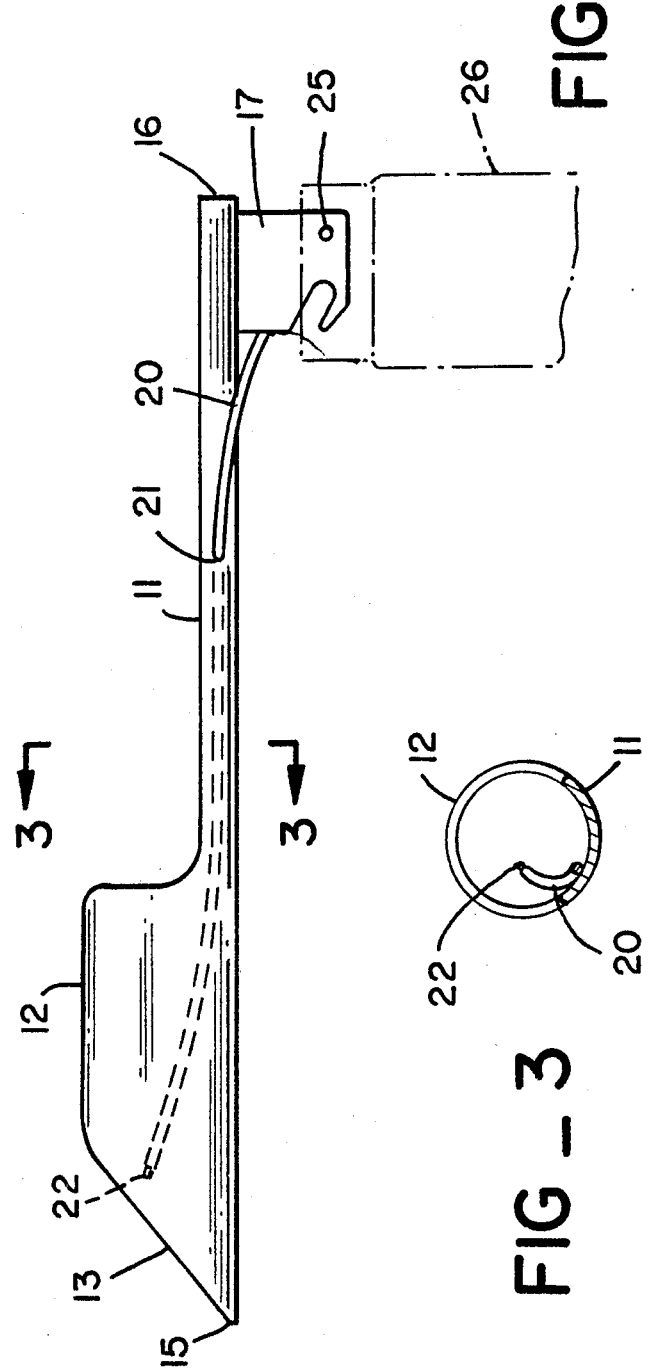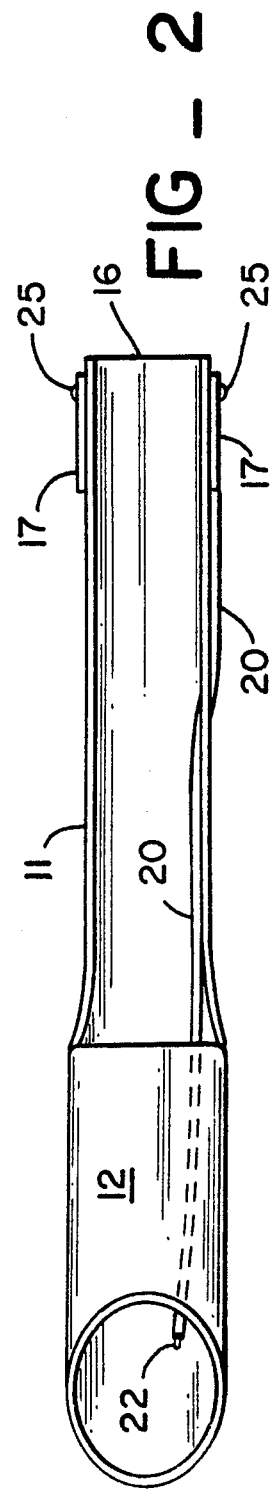

LARYNGOSCOPE FOR USE WITH PHARYNGEAL OBSTRUCTIONS

FIELD OF THE INVENTION

This invention is in the field of laryngoscopes.

BACKGROUND OF THE INVENTION

Obstruction within a person's upper air passageway may be life threatening. If the obstruction is substantially complete some action to remove or to bypass the obstruction must be taken within three to four minutes or the person will die. Obstruction can occur for many reasons one of which is edema of the pharynx. The pharynx has a soft inner tissue to which body liquids can gravitate to cause edema. Edema can be caused by neck trauma, surgery in the region of the upper air passages, allergic reactions or bleeding in regions near the pharynx, among other causes. When the upper air passage is blocked a person's life may be saved by installing an endotracheal tube, however the swollen pharyngeal area makes it very difficult to pass a tube through the pharynx and impossible to see the part of the larynx through which the tube must pass.

To install an endotracheal tube in an emergency situation it is almost always necessary to have a laryngoscope and some means for illuminating the area of the larynx into which the endotracheal tube must be inserted. A laryngoscope normally has a long blade connected through a hinge-like mechanism to a handle. The handle usually contains batteries and some illumination source which is directed toward the area at the end of the laryngoscope blade. A light source frequently is an incandescent bulb electrically connected to the batteries in the handle. Alternatively, illumination can be provided by sources in the handle that shine into the end of a fiberoptic bundle which passes down the blade to provide illumination at its tip.

Laryngoscope blades come in many shapes. Most of them are elongated blades having a trough-shaped cross section while others are tubular or have a tubular shape with a slit in the tube along one side. Other laryngoscopes have curved blades which follow the shape of the air passageway from a person's mouth to the larynx. Examples of blades of these types can be found in U.S. Pat. Nos. 4,295,465 to Racz; 4,337,761 to Upsher and 3,856,001 to Phillips.

It has been found that when the pharynx suffers serious edema, the tissue is so soft and swollen that it will conform to the shape of the laryngoscope blade. The swollen pharynx will fill the trough of an open blade and will enter any slits or other openings of a partially closed tubular blade. The swollen pharynx thereby not only obstructs the ability to view the larynx directly but it also interferes with the ability to illuminate the area of the larynx.

Tubular blades are available which can displace edematous pharyngeal tissue. Unfortunately existing tubular blades are difficult to use in emergency situations because a patient's jaw and teeth restrict the amount of manipulation that can be performed with a continuous tubular blade. In addition, it is difficult to manipulate instruments or tubes within the long, restricted tubular passageway. Tubular blades are generally used with heavy light sources which are not easily transported and thus not available in emergency situations. Thus, none of the known laryngoscope blades has been found to be satisfactory in dealing with airway emergencies caused by pharyngeal edema.

SUMMARY OF THE INVENTION

The laryngoscope blade of this invention is a straight blade which is defined herein as a blade having substantially no front-to-back curvature and one that a user can sight along from one end to the other without the blade, itself, causing obstruction to vision. One end of the blade is provided with a means to connect with an ordinary laryngoscope handle and to provide a means to make an electrical connection with the handle, as is known to the art. The portion of the blade adjacent to the end connecting to the handle is trough-shaped in cross section and it extends to and is integral with the other end of the blade which is tubular. The tubular end of the blade is beveled toward its end and includes within it a light source that produces a diverging pattern of light. Preferably the interior of the tubular portion is shiny to reflect as much light as possible.

The tubular portion of the blade, including the beveled portion, is between 5 and 8.5 centimeters long. A tubular portion of that length will exclude virtually all swollen pharynx tissue from the line of sight down the blade of this invention. A tubular portion that is longer than 8.5 centimeters restricts the ability to manipulate the device and it additionally interferes with the ability to manipulate other tools or equipment within the interior of the tubular portion.

BRIEF DESCRIPTION OF THE DRAWINGS

FIG. 1 is an elevation view of a laryngoscope blade embodying this invention.

FIG. 2 is a plan view of the blade illustrated in FIG. 1.

FIG. 3 is a cross-section of the blade illustrated in FIG. 1 taken along the line 3—3 in the direction of the arrows.

DETAILED DESCRIPTION OF THE INVENTION

The drawings illustrate a laryngoscope blade embodying the invention. The laryngoscope blade includes a trough-shaped portion 11 and tubular portion 12. The tubular portion 12 has a beveled or slanted end opening 13 that terminates in a smoothly rounded point 15. The slanted opening 13 and rounded point 15 make it easy for tubular portion 12 to be maneuvred through swollen pharynx tissue even when the tissue is swollen to the extent that a patient's breathing is completely obstructed. The end of the trough-shaped portion 16 is connected to a means 17 that is adapted to connect the laryngoscope blade to a handle shown in broken lines and generally designated 26. Such connections are known to be useful with laryngoscope blades.

The attachment means 17 is conventional and it includes contact points 25 which coact with corresponding contact points within handle 26 so that batteries contained in handle 26 may be used to energize a light source within the laryngoscope. The leads to the light source are within a tube 20 which passes through a diagonally cut opening 21 in the side wall of trough-like portion 11 and passes against the inner wall of the trough-like portion 11 until tube 20 enters tubular portion 12. In the illustrated embodiment an incandescent bulb 22 is fixed in the end of tube 20 and beyond the opening of the tubular portion 12 although it is behind the sloping portion 13 whereby light source 22 is available to be grasped and changed if necessary but it is still protected from direct contact with tissue. Tube 20 is also bent so that light source 22 is not immediately adjacent the interior wall of tubular portion 12.

In use, for example in an emergency room or by a paramedic at the site of a medical emergency, if a patient has such sever edema of the pharynx that he is unable to breath, the laryngoscope of this invention may be assembled very quickly onto handle 26 by snapping the adaptor 17 onto the handle. All medically trained personnel are familiar with this technique and can normally do it in a fraction of a second. With handle 26 in place contacts 25 may be energized by the batteries in handle 26 and source 22 may become illuminated. The mouth of the patient is then opened and with familiar manipulations of the laryngoscope the tip 15 is manipulated so that tubular portion 12 passes through the swollen pharynx thereby immediately relieving the patient's inability to breath.

A normal pharynx, whether swollen or not, will not extend to the front of or to the back of the tubular portion 12. With the emergency relieved, an endotrachael tube can easily be passed through tubular portion 12 and with the general illumination of the larynx the tube can be inserted into the trachea of the patient so that when the laryngoscope tube is removed from the patient a breathing passageway will remain. The laryngoscope also can accomodate tools for grasping and removing foreign objects lodged in the throat of a patient as well as dealing with other injured portions of the patient that are concealed by a swollen pharynx.

The creation of viewing space and the general and diffused illumination provided by source 22 is an important feature of the laryngoscope of this invention. Although the invention is illustrated showing a small, incadescent bulb, any small, bright source of illumination may be employed with equivalent results. If fiberoptic bundles are used the fiberoptic bundle may pass through tube 20 instead of wires, and the illumination source that shines into the remote end of the fiberoptic bundle may be in the handle 26. In addition, it is evident from FIG. 1 that the low profile of trough-like portion 11 permits the blade to be maneuvred with minimum interference from a patient's teeth or jaws and it also evident that the limited front t back extent of tubular portion 12 provides minimum restriction for manipulating tubes or other surgical tools that are to function beyond the end of tubular portion 12.

What is claimed is:

1. A laryngoscope blade comprising a first end including means to attach to a handle, a tubular portion beveled to a second end, a trough-shaped portion berween said first end and said tubular portion, said tubular portion being between 5 centimeters and 8.5 centimeters long, and illumination means in the interior of said tubular portion.

2. The device of claim 1 having an electrical contact on said means attachable to a handle.

3. The laryngoscope blade of claim 1 including a handle with means to attach to said blade and with an electrical contact positioned to create a circuit with an electric contact positioned at the first end of said blade.

* * * * *